(12) United States Patent
Rawls

(10) Patent No.: US 8,641,677 B2
(45) Date of Patent: Feb. 4, 2014

(54) LOW-PROFILE INTRAVENOUS CATHETER DEVICE

(76) Inventor: James T. Rawls, Folly Beach, SC (US)

( * ) Notice: Subject to any disclaimer, the term of this patent is extended or adjusted under 35 U.S.C. 154(b) by 0 days.

(21) Appl. No.: 12/657,471

(22) Filed: Jan. 21, 2010

(65) Prior Publication Data

US 2011/0178464 A1    Jul. 21, 2011

(51) Int. Cl.
*A61M 5/178* (2006.01)
*A61M 25/00* (2006.01)

(52) U.S. Cl.
USPC ............. 604/168.01; 604/164.01; 604/523; 604/524

(58) Field of Classification Search
USPC ............... 604/168.1, 164.01, 164.04, 604/170.01–170.02, 523–524, 526–528, 604/168
See application file for complete search history.

(56) References Cited

U.S. PATENT DOCUMENTS

| | | | |
|---|---|---|---|
| 3,059,645 A | | 10/1962 | Hasbrouck et al. |
| 3,565,074 A | * | 2/1971 | Foti .................... 604/164.11 |
| 3,853,126 A | | 12/1974 | Schulte |
| 3,942,528 A | * | 3/1976 | Loeser ..................... 604/174 |
| 4,368,730 A | * | 1/1983 | Sharrock ................... 604/158 |
| 4,417,886 A | | 11/1983 | Frankhouser et al. |
| 4,431,426 A | * | 2/1984 | Groshong et al. ........... 604/523 |
| 4,453,933 A | * | 6/1984 | Speaker .................. 604/179 |
| 4,496,348 A | * | 1/1985 | Genese et al. ........... 604/167.02 |
| 4,516,972 A | * | 5/1985 | Samson .................... 604/526 |
| 4,606,735 A | | 8/1986 | Wilder et al. |
| 4,644,960 A | | 2/1987 | Johans |
| 4,711,636 A | | 12/1987 | Bierman |
| 4,737,153 A | * | 4/1988 | Shimamura et al. .......... 604/526 |
| 4,894,052 A | | 1/1990 | Crawford |
| 4,895,561 A | | 1/1990 | Mahurkar |
| 4,936,826 A | * | 6/1990 | Amarasinghe ............. 604/507 |
| 4,976,698 A | * | 12/1990 | Stokley .................... 604/174 |
| 5,053,023 A | * | 10/1991 | Martin ..................... 604/523 |
| 5,101,682 A | | 4/1992 | Radisch, Jr. et al. |
| 5,116,324 A | * | 5/1992 | Brierley et al. ............. 604/180 |
| 5,147,320 A | | 9/1992 | Reynolds et al. |
| 5,156,592 A | | 10/1992 | Martin et al. |
| 5,205,830 A | | 4/1993 | Dassa et al. |
| 5,246,426 A | | 9/1993 | Lewis et al. |
| 5,319,152 A | * | 6/1994 | Konishi ..................... 84/637 |

(Continued)

OTHER PUBLICATIONS

International Search Report from PCT/US2011/021635—3 pages.

(Continued)

*Primary Examiner* — Quynh-Nhu H Vu
(74) *Attorney, Agent, or Firm* — Dority & Manning, P.A.

(57) ABSTRACT

An intravenous catheter device and system includes: (a) a medical tubing connector at a first end of the intravenous catheter device; (b) a length of flexible, non-kinking, supported medical tubing, a first end of the non-kinking tubing being connected to a first end of the medical tubing connector; (c) an intravenous catheter portion having a first end attached to a second end of the non-kinking tubing, the non-kinking tubing extending between the intravenous catheter portion and the tubing connector; and (d) a cylindrical-shaped cuff attached to a first outside end portion of the intravenous catheter portion, and a second outside end portion of the non-kinking tubing; wherein a central channel of the intravenous catheter portion is in fluid communication with a channel of the non-kinking, flexible tubing when the intravenous catheter device is in use. This simplified abstract is not intended to limit, and should not be interpreted as limiting, the scope of the claims.

11 Claims, 5 Drawing Sheets

(56) References Cited

U.S. PATENT DOCUMENTS

| | | | |
|---|---|---|---|
| 5,330,432 A * | 7/1994 | Yoon | 604/164.12 |
| 5,342,317 A * | 8/1994 | Claywell | 604/179 |
| 5,417,208 A | 5/1995 | Winkler | |
| 5,443,460 A * | 8/1995 | Miklusek | 604/530 |
| 5,555,618 A | 9/1996 | Winkler | |
| 5,577,516 A | 11/1996 | Schaeffer | |
| 5,601,539 A | 2/1997 | Corso, Jr. | |
| 5,607,407 A | 3/1997 | Tolkoff et al. | |
| RE35,924 E | 10/1998 | Winkler | |
| 5,913,852 A * | 6/1999 | Magram | 604/540 |
| 5,916,199 A * | 6/1999 | Miles | 604/174 |
| 6,001,081 A | 12/1999 | Collen | |
| 6,045,734 A | 4/2000 | Luther et al. | |
| 6,117,108 A | 9/2000 | Woehr et al. | |
| 6,190,370 B1 | 2/2001 | Tsui | |
| 6,277,103 B1 | 8/2001 | Lauer | |
| 6,287,278 B1 | 9/2001 | Woehr et al. | |
| 6,456,874 B1 | 9/2002 | Hafer et al. | |
| 6,508,806 B1 * | 1/2003 | Hoste | 604/524 |
| 6,740,063 B2 | 5/2004 | Lynn | |
| 6,893,056 B2 | 5/2005 | Guala | |
| 6,939,337 B2 | 9/2005 | Parker et al. | |
| 6,955,669 B2 | 10/2005 | Curutcharry | |
| 6,969,375 B2 | 11/2005 | Thibault et al. | |
| 6,973,346 B2 | 12/2005 | Hafer et al. | |
| 7,137,990 B2 | 11/2006 | Hebert et al. | |
| 7,198,066 B2 * | 4/2007 | Kagenow | 138/110 |
| 7,297,302 B2 | 11/2007 | Berg et al. | |
| 7,386,341 B2 | 6/2008 | Hafer et al. | |
| 7,678,083 B2 * | 3/2010 | Stephens | 604/174 |
| 2003/0229294 A1 | 12/2003 | Bailey et al. | |
| 2005/0011568 A1 | 1/2005 | Kagenow | |
| 2005/0015072 A1 * | 1/2005 | Engel et al. | 604/523 |
| 2005/0165366 A1 | 7/2005 | Brustad et al. | |
| 2005/0215953 A1 | 9/2005 | Rossen | |
| 2005/0234405 A1 | 10/2005 | Dikeman et al. | |
| 2006/0015068 A1 | 1/2006 | Amisar et al. | |
| 2008/0300574 A1 | 12/2008 | Belson et al. | |
| 2008/0312611 A1 * | 12/2008 | Racz | 604/272 |
| 2008/0319387 A1 | 12/2008 | Amisar et al. | |
| 2011/0040281 A1 | 2/2011 | White | |

OTHER PUBLICATIONS

M29 Midterm Product Information at www.flexicath.com—2 pages.
NovaCath Product Information at tangentmedical.com—1 page.
PiccWand Product Information at the-wand.com—1 page.
Vascular Pathways RIVS System Product Information at www.mvmlifescience.com—1 page.

* cited by examiner

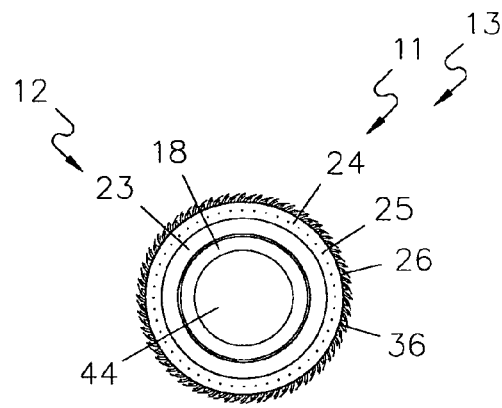
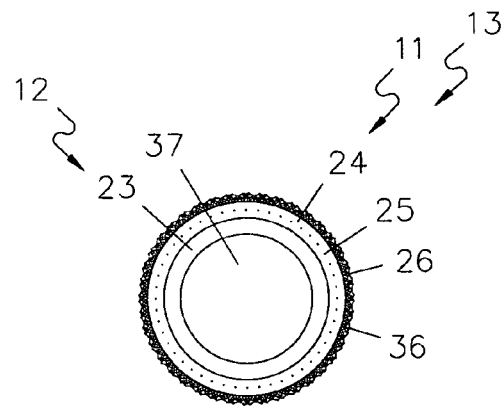
Fig. 5
Fig. 7
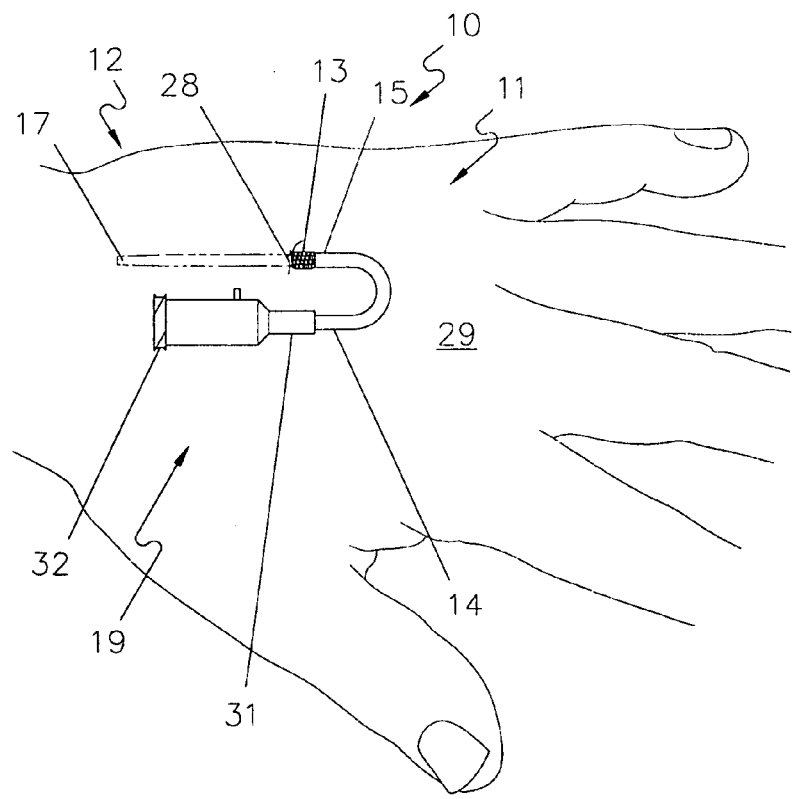
Fig. 6

LOW-PROFILE INTRAVENOUS CATHETER DEVICE

BACKGROUND OF THE INVENTION

1. Technical Field

The present invention relates to a low-profile, non-kinking intravenous catheter device that includes a section of flexible yet supported intravenous tubing for conducting fluids into a patient's blood vessel or the like.

2. Background Information

Various types of intravenous ("IV") catheters are well known in the medical field and are used throughout the world. Intravenous catheters are used for a wide variety of applications, including hydration and administration of intravenous fluids, medications, feeding, and transfusions. A typical intravenous system utilizes a needle for penetrating the skin and vein, and a catheter that remains in the patient's blood vessel for a time once the needle is removed. A catheter is a cylindrical tube made of a thin, stiff plastic-type material. The intravenous catheter slides over the needle into the vein once the needle has punctured the vein. The needle is then removed, leaving the intravenous catheter in place in the vein. There are a variety of needle safety systems in use by various catheter manufacturers, which automatically cover the sharp tip of the needle as it is removed from the catheter and discarded. The intravenous catheter is then connected to medical tubing via a screw-type or other type of tubing connector. A saline solution is then normally used to flush the catheter and test for proper placement of the intravenous catheter in the blood vessel.

Once placement in the patient's blood vessel has been confirmed, the intravenous catheter is secured to the patient's skin with adhesive tape until it is time to remove the IV, until the IV is accidentally dislodged or damaged, or until the vein blows. The latter term ("blows") is a common term for extravasation of the intravenous fluids and/or blood into the space outside of the vein, i.e., when the seal between the vein and the catheter becomes leaky and fluid being administered thorough the catheter goes partly into the vein and partly under the skin. Unfortunately, this happens frequently because of the fact that the veins that are most accessible to health care professionals are the ones in the patient's hand, wrist, and inner elbow (antecubital fossa), where there is much movement. The catheter of a conventional IV system is prone to being inadvertently bumped, snagged, and hit on objects because of the way the regular tubing that leads to the medical fluid source is commonly looped. This is especially true pre- and post-surgery, when patients often must be moved, and when the administration of anesthetic drugs via intravenous catheters can be critical. Loss of IV access can pose very serious problems if it occurs at the wrong time or with the wrong medication, for example.

Some external devices have been invented over the years that, for example, clasp over or are strapped to an intravenous catheter, but the above-described problems associated with the use of intravenous catheters persist. Various other catheter-related patents and publications relate to, for example: an instrument and method for delivery of anesthetic drugs; a catheter with a high tensile strength braid wire constraint; a manipulative delivery catheter for occlusive devices; an electrode-carrying catheter; medical tubing; and a multilayered polymeric tubing with braided layer; and methods of making and using them and a process of making a catheter. The intravenous catheter device of the present invention with its section of flexible yet supported intravenous tubing is bendable into a low-profile conformation so that the present intravenous catheter device is less likely to kink or be dislodged from the patient's vessel.

BRIEF SUMMARY OF THE INVENTION

The present invention is a low-profile, non-kinking intravenous catheter device, which comprises: (a) a medical tubing connector at a first end of the intravenous catheter device; (b) a length of flexible, non-kinking, supported medical tubing, a first end of the non-kinking tubing being connected to a first end of the medical tubing connector; (c) an intravenous catheter portion at an opposite, second end of the intravenous catheter device, a first end of the intravenous catheter portion being attached to a second end of the non-kinking tubing, the non-kinking tubing extending between the intravenous catheter portion and the tubing connector; and preferably (d) a cylindrical-shaped cuff attached to a first outside end portion of the intravenous catheter portion adjacent the first catheter portion end, and a second outside end portion of the non-kinking tubing adjacent the second end of the non-kinking tubing. A central channel of the intravenous catheter portion is in fluid communication with a channel of the non-kinking, flexible tubing when the intravenous catheter device is in use. Although the non-kinking medical tubing is preferably wire-supported, the tubing support arrangement may be formed of plastic or other suitable medical grade material. A catheter system including the intravenous catheter device and a needle/flash chamber unit is also included herein.

Advantages of the intravenous catheter device and system of the present invention include the following: 1) permits safe and comfortable infusion of intravenous fluids into a patient; 2) permits movement of the patient's joints without causing kinking of the catheter tubing or dislodgement of the intravenous catheter; 3) includes a length of non-kinking tubing that can be bent into an appropriate shape on the patient's body part so that the present intravenous catheter device maintains a low-profile against the patient's body; 4) decreases the likelihood that a combative patient will have to be restrained because of concern about dislodgement of the patient's intravenous catheter; 5) significantly decreases expenses associated with kinking of catheter tubing and dislodgement of intravenous catheters, such as expenses associated with restarting IVs, combating infections that start around the catheter site, delayed surgeries, patient injuries, extended hospital stays, and even deaths; 6) one less concern for surgical staff before, during, and after surgery; and 7) does not require additional equipment or training of healthcare personnel in order to use it. The above advantages are particularly true of the pediatric population because of their tendency to move about more than adult patients.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein:

FIG. 5 is a cross-sectional view of a cuff connector of the intravenous catheter device of FIG. 3, taken across line 5-5;

FIG. 6 is an elevational view of an intravenous catheter device according to the present invention;

FIG. 7 is a cross-sectional view of a cuff connector of the intravenous catheter device of FIG. 4, shown without a needle and taken across line 7-7;

DETAILED DESCRIPTION OF THE INVENTION

Figure 1:
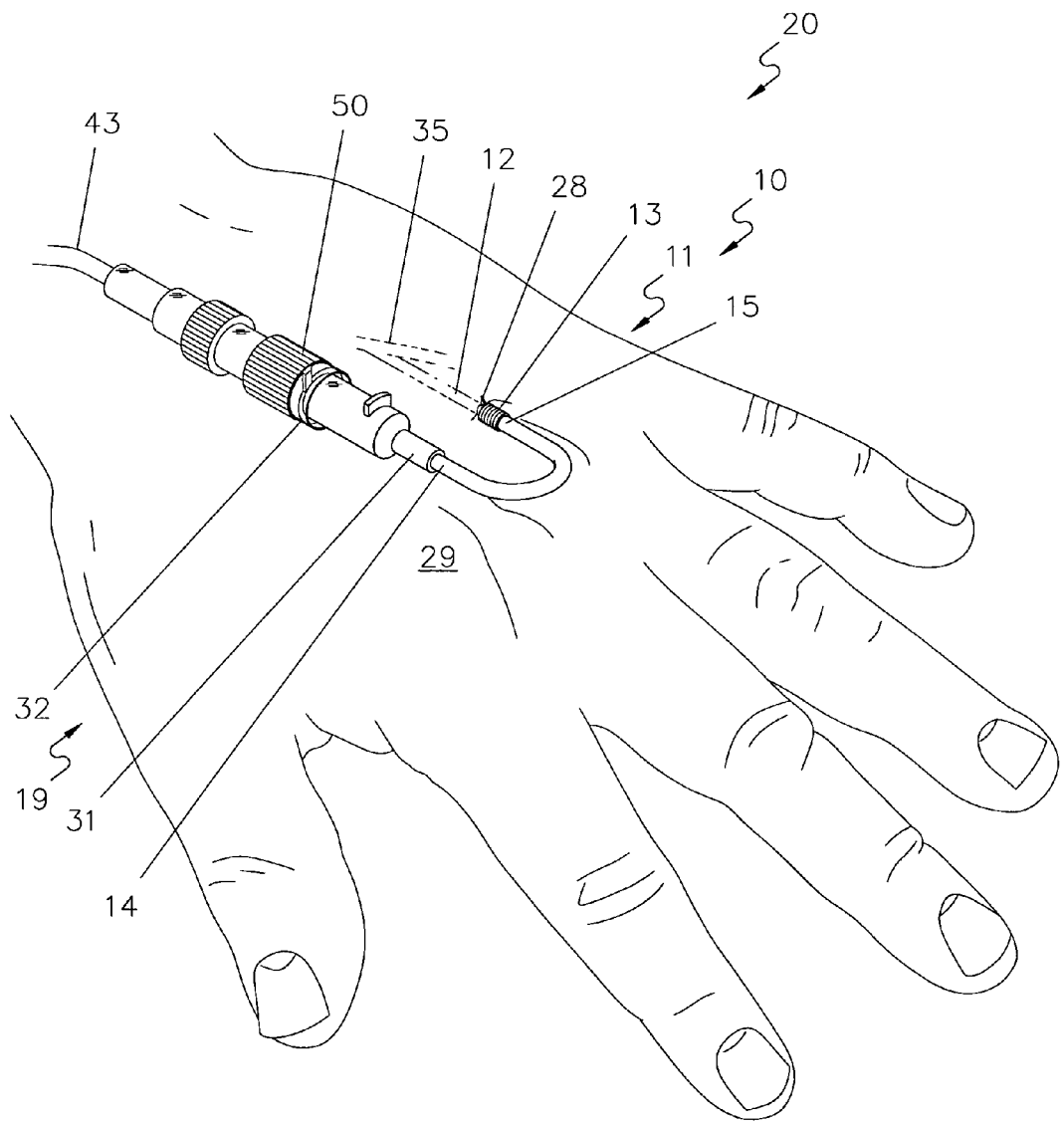
FIG. 1 shows a perspective view of an intravenous catheter device according to the present invention, shown on a patient's hand.

In the following description, like reference characters designate like or corresponding parts throughout the several views. Also, in the following description, it is to be understood that such terms as "over," "under," "within," and the like are words of convenience and are not to be construed as limiting terms. Referring in more detail to the drawings, a device embodying the principles and concepts of the present invention and generally designated by the reference numeral 10 will now be described.

Turning first to FIGS. 1 through 4, an intravenous catheter device 10 herein comprises: (a) a medical tubing connector, preferably a leak-free screw-type connector 19; (b) a length of flexible, non-kinking, supported medical tubing 11, a first end 14 of which is connected to a first end 31 of the screw-on connector 19; (c) an intravenous catheter portion 12 at an opposite, second end of the intravenous catheter device 10, a first end 16 of which is connected to a second end 15 of the length of non-kinking tubing 11, the non-kinking tubing 11 extending between the intravenous catheter portion 12 and the tubing connector 19; and preferably (d) a cylindrical-shaped cuff 13 connected to the first outside end portion 53 at the first end 16 of the intravenous catheter portion 12 and the second outside end portion 54 towards the second end 15 of the non-kinking tubing 11. A preferred non-kinking tubing 11 for use herein is wire-supported, though it does not have to be wire-supported. The tubing support arrangement may alternatively be formed of plastic or other suitable medical grade material.

The intravenous catheter device 10 preferably also includes: (e) a removable needle 18 comprising a second, pointed end 34 for piercing the patient's skin and blood vessel. The needle 18, which slides within the intravenous catheter portion 12 and the non-kinking tubing 11, is removed from the intravenous catheter device 10 once the second end 17 of the intravenous catheter portion 12 is placed within the lumen of the patient's vein 35. The first, non-piercing end 33 of the needle 18 is preferably connected to a flash chamber 27. Once the intravenous catheter device 10 is in use, the channel 22 of the intravenous catheter portion 12 is in fluid communication with the channel 37 of the non-kinking tubing 11. Preferably, the non-kinking tubing channel 37 is in fluid communication with the channel 38 in the medical tubing (preferably screw-on) connector 19, which is in fluid communication with a channel of the regular IV fluid tubing 43 above the screw-on connector 19. The upper end of the IV fluid tubing 43 is connected to the IV bag or other source of medical fluid to be administered to the patient via the intravenous catheter device 10.

Figure 2:
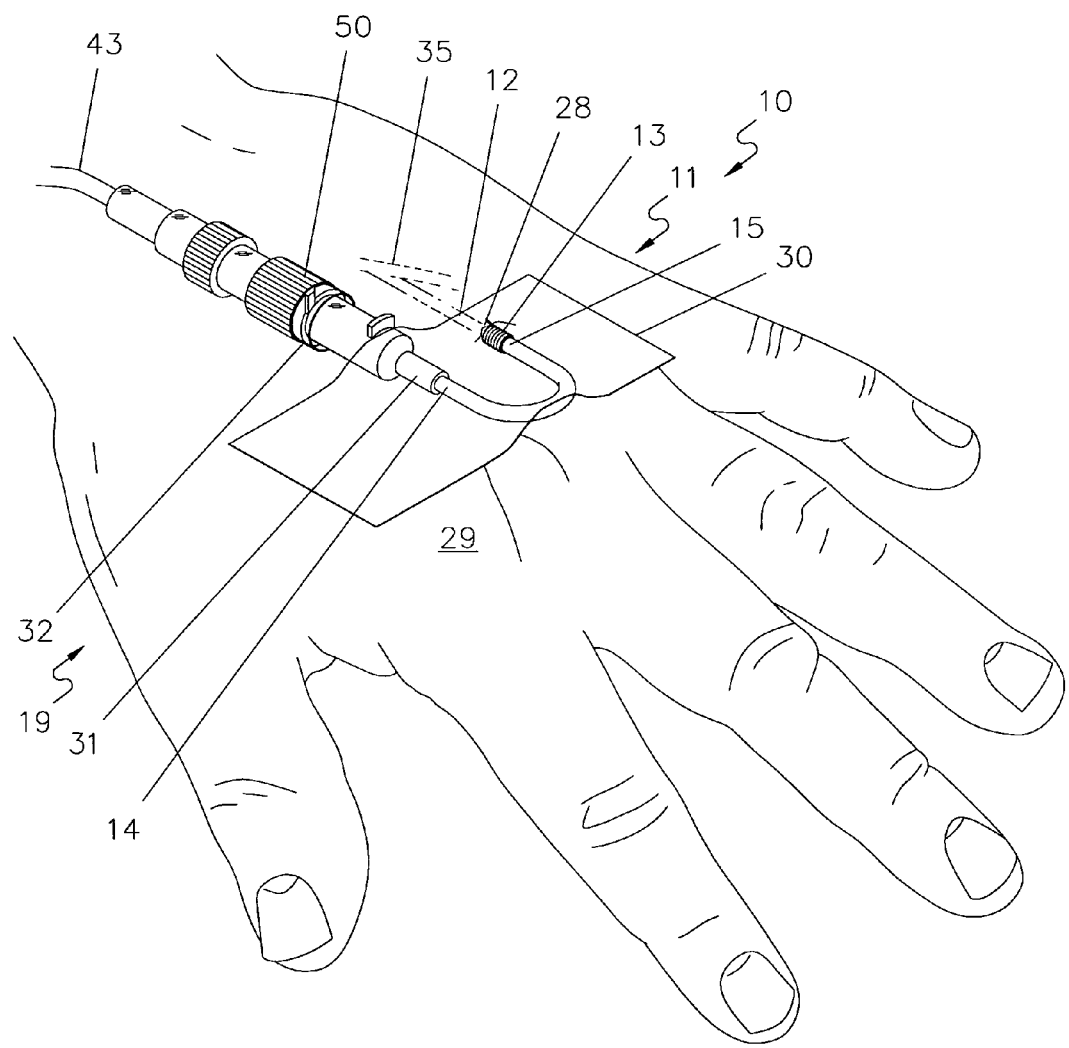
FIG. 2 is a perspective view of an intravenous catheter device according to the present invention, shown with adhesive tape and ready for use.

Importantly, the flexible, non-kinking tubing 11 of the intravenous catheter device 10 depicted in FIGS. 1, 2, and 6 permits the intravenous catheter device 10 to remain in position on the patient once the intravenous catheter device 10 has been placed and the non-kinking, flexible tubing 11 is bent into place by the healthcare professional. The bent non-kinking tubing 11 also permits the intravenous catheter device 10 to maintain a low profile against the patient's limb. The section of non-kinking tubing 11 is not the same as the IV fluid tubing 43 up above the screw-on connector 19, which leads up to the source of the fluid/medication to be administered to the patient through the intravenous catheter device.

Since the most easily accessed, best veins are found inside the elbows or wrists of the majority of relatively healthy patients, an intravenous catheter is frequently placed there. If necessary, the intravenous catheter may also be placed on the patient's hand, thumb, ankle, scalp, belly button, foot, leg, chest, or wherever a promising site can be found on the patient's body. Unfortunately, these IV positions are uncomfortable at a minimum, and can even be dangerous if the intravenous catheter is jostled out of place or if the medical tubing is kinked sufficiently to inhibit flow of the medicine or other fluids passing through the intravenous catheter device. Even though the intravenous catheter device 10 is likely to be placed near a patient's joint, it is not likely to be jostled out of place, or to kink. An intravenous catheter device 10 placed at the wrist, for example, maintains a low profile, even though it is taped down on the arm in a "J" or "U" shape. The catheter portion is less likely to kink or be dislodged from the patient's vessel. An intravenous catheter device 10 placed inside the elbow (in the antecubital fossa), for example, can be taped down without bending it into a U-shape. The catheter device is not likely to kink or be dislodged, because the non-kinking supported tubing 11 (rather than the catheter portion) flexes as the patient bends his or her elbow and otherwise moves his or her arm. The non-kinking tubing 11 can bend and re-bend in different directions without kinking as it moves rather fluidly with the patient's movements.

As seen in FIGS. 1 and 2, the needle 18 has been removed from the intravenous catheter device 10 prior to administration of the IV fluids through the intravenous catheter device 10, and the non-kinking tubing portion 11 has been turned while maintaining a low profile. It can also be seen that the screw-type connector 19 has been attached to IV fluid tubing 43 for the administration of the IV fluids with or without medications.

Any suitable, medical grade metal, plastic, or nylon fiber material can be used to support the wall 24 of the non-kinking tubing 11, so long as the support material does not compromise flexibility of the section of non-kinking tubing 11. For example, a length of fine, medically safe wire 25 can be incorporated within the tubing material. The non-kinking tubing 11 is preferably molded from a relatively flexible, medical grade plastics material with a section or sections of a fine, surgical wire 25 encapsulated within the plastic material in the wall of the flexible tubing. By "surgical wire" is meant that the wire 25 is suitable for use within the human body. By "medical grade" is meant the material can safely be used in or on the human body. The flexible tubing material does not melt at temperatures within human body temperature range (around 37 degrees Centigrade).

Figure 8A:
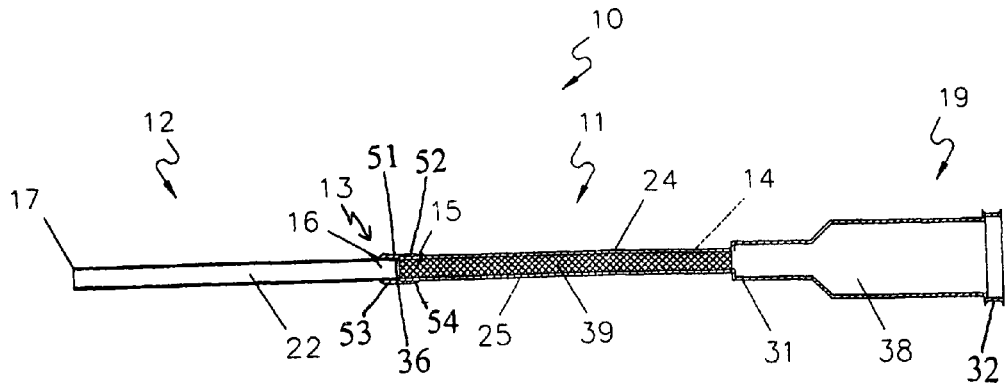
FIG. 8A is a cross-sectional view of the intravenous catheter device according to FIG. 4, taken across line 8-8 and shown with a mesh tubing support arrangement.
Figure 8B:
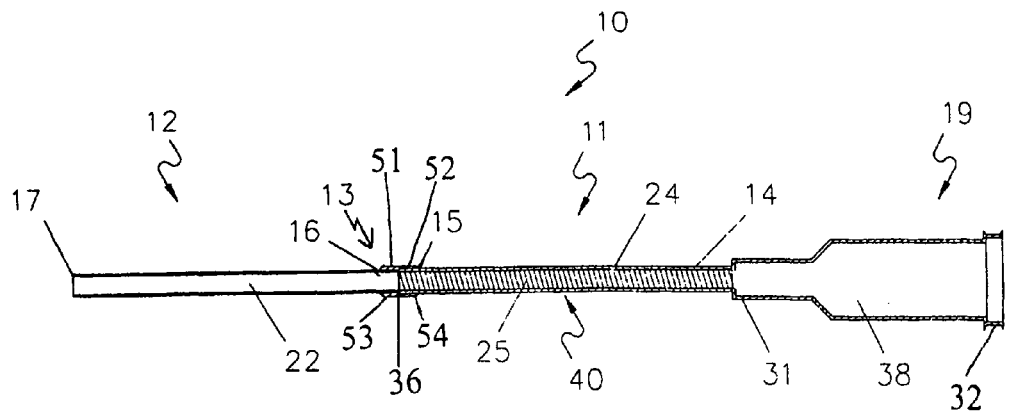
FIG. 8B is a cross-sectional view of the intravenous catheter device according to FIG. 4, taken across line 8-8 and shown with a spiral tubing support arrangement.
Figure 8C:
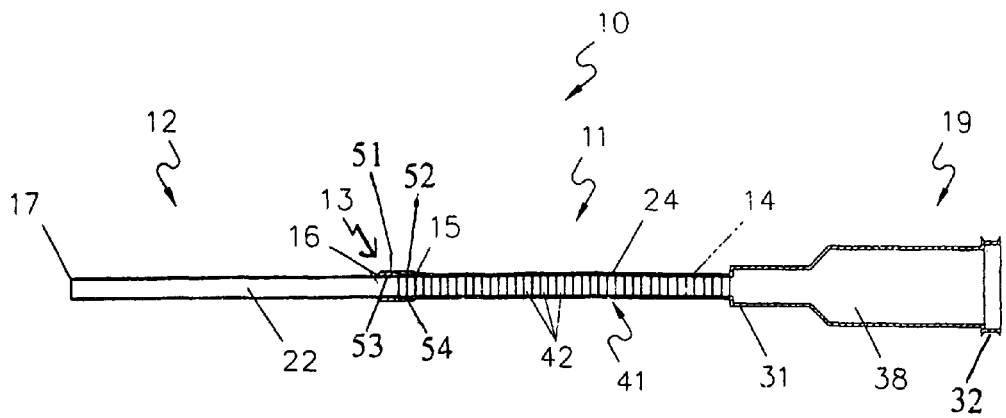
FIG. 8C is a cross-sectional view of the intravenous catheter device according to FIG. 4, taken across line 8-8 and shown with a ring tubing support arrangement.

The non-kinking tubing 11 is a smooth bore, non-compressing, flexible tubing. There are several materials that can be used, including, but not limited to, wire-reinforced tubing, and nylon fiber tubing. The non-kinking tubing 11 may be supported by any suitable material that conveys sufficient stiffness to the non-kinking tubing 11 for the intravenous catheter to be pushed in and pulled out short distances, which in turn moves the catheter portion 12 under the skin, yet maintains sufficient flexibility for the non-kinking tubing 11 to be bent (into a J- or U-shape) without collapsing or kinking. Alternate tubing support arrangements within the non-kinking tubing wall 24 are seen in FIGS. 8A-C. Where the tubing material is transparent or translucent, the tubing support arrangement 39-41 is visible to the naked eye. In the non-kinking tubing 11 shown in FIGS. 8A-C in particular, the fine, surgical grade wire 25 is visible within the transparent wall of the non-kinking tubing 11. (The non-kinking tubing 11 need not be transparent, though.) The wire 25 is preferably entirely enclosed within the plastic or other material of the non-kinking tubing 11, so the wire 25 is unlikely to cause any problems reacting with fluids of the human body.

In regard to FIG. 8A, one preferred tubing arrangement is the mesh support arrangement 39 that is also seen in cross-section FIGS. 5 and 7. A particularly preferred mesh support arrangement 39 is a fine wire screen. The mesh extends the length of the non-kinking tubing 11 within the tubing wall 24. The mesh support arrangement 39 may alternatively be formed of a piece or pieces of fine plastic netting. The mesh support structure is believed to provide effective support for the non-kinking tubing 11, particularly when bending the non-kinking tubing into the desired shape after the intravenous catheter device 10 has been inserted and the needle 18 has been retracted.

A second example is the coiled, or spiral, tubing support arrangement 40 shown in FIG. 8B. The particular coil arrangement depends in part upon the properties of the wire 25 that is used. In a preferred support arrangement, the fine wire 25 of the spiral arrangement 40 is tightly and evenly coiled around the non-kinking tubing channel 37 within the tubing wall 24 as seen in FIG. 8B. It is believed that this tight and even coiling arrangement keeps the non-kinking tubing channel 37 from collapsing when the non-kinking tubing 11 is bent, yet permits the non-kinking tubing 11 to flex as needed. The coils extend from one end of the length of tubing to the other. The individual coils are preferably close/adjacent to one another. A less preferred embodiment includes loose, spaced apart spirals. A fine wire-shaped plastic support can be used in place of the fine wire, if desired, when the non-kinking tubing 11 is made. The plastic spiral support arrangement 40 has the same appearance seen in FIG. 8B. Other suitable support materials may be used in place of fine wire or plastic.

Thirdly, the ring support arrangement 41 shown in FIG. 8C is made up of a number of wire or plastic support bands, or rings 42. The generally cylindrical-shaped support rings 42 are either adjacent one another or spaced apart from one another along the length of the non-kinking tubing 11. The support rings 42 are contained within the tubing wall 24. Thus, the inside diameter of the individual support rings 42 is only slightly less than the outside diameter of the non-kinking tubing 11. The individual support rings 42 are not so wide that they interfere with the capacity of the non-kinking tubing 11 to bend into the U-shape or J-shape when the intravenous catheter is in use. The individual support rings 42 of FIG. 8B are same-sized, and spaced apart substantially the same distance from one another (so that every other band in FIG. 8B is a ring 42). It is believed that this even ring arrangement 41 of small rings 42 both prevents the non-kinking tubing channel 37 from collapsing when the non-kinking tubing 11 is bent, and permits the non-kinking tubing 11 to flex as needed. The support rings 42 of the ring support arrangement 41 may be made of plastic or metal, which have the same appearance as shown in FIG. 8C. The support rings 42 may alternatively be made of any other material that is found to be suitable.

The dimensions of the substantially thin, flexible tubing wall, and the diameter of the substantially uniform tubing channel within the flexible tubing 11, may vary. In general, the length of the non-kinking, flexible tubing 11 is determined by the diameter of the intravenous catheter portion 12 of the intravenous catheter device 10, as well as the relative flexibility of the non-kinking tubing 11, which is appropriately matched to the intravenous catheter portion 12.

It can be appreciated that it is difficult to maintain an open channel over time between the end of a relatively stiff, man-made catheter and the lumen of a slippery human vein. Intravenous catheter tubing often becomes entangled or is simply pulled out of the vein, particularly when the patient is an active child. Fluids from a dislodged catheter often quickly infiltrate the patient's tissue under the integument and cause localized swelling. Sometimes simple movements by the patient or attendant cause the medical tubing to kink, which shuts off the flow of fluids through the tubing to the patient's blood supply. The present intravenous catheter device 10 helps prevent the common and sometimes critical problem of intravenous catheter entanglement, dislodgement, and/or kinking by providing a flexible, non-kinking tubing 11 between the intravenous/drip catheter portion 12, which remains in the lumen of the patient's blood vessel 35, and the screw-type connector 19. Although the non-kinking tubing 11 is in fluid connection with the intravenous catheter portion 12, the non-kinking, flexible tubing 11 and the screw-type connector 19 remain outside the patient's skin (not inside the body).

The intravenous catheter device 10 is placed into the patient's vein 35 using a conventional technique for inserting an intravenous catheter: the skin and vein are penetrated using a sharp, specialized needle 18 and the catheter is then introduced into the lumen of the vein 35. Finally, the needle 18 is withdrawn from the vein 35, leaving the intravenous catheter portion 12 in place in the lumen of the vein 35. The needle 18 is also called a cannula.

By "non-kinking" is meant that the flexible tubing does not kink even when it is twisted into a U-shape. By "medical" is meant that the flexible tubing has been approved as safe for medical uses; fluids like Ringer's lactate solution, normal saline solution, medicines, or blood from a blood bank can pass through the non-kinking, flexible tubing into the blood stream of the patient without undue risk of blood clotting, bacterial growth, or introduction of foreign bodies, for example.

The intravenous catheter device 10 includes the intravenous catheter portion 12. The intravenous catheter 12 itself is a small, thin walled, relatively stiff medical grade plastic tube used for conducting fluids, such as medications, sugar/salt solutions, or nutrients, to a vessel of a patient's body.

At the point of attachment between the IV catheter and the flexible, non-kinking tubing 11 is a cylindrical-shaped cuff 13, preferably antibacterial. The purpose of the cuff is to help prevent or absorb any leakage of blood and, importantly, to provide a substrate on which the adhesive dressing attaches. A preferred cuff 13 includes short cuff fibers 26, which increase surface area. The cuff 13 is preferably made of fibrous polyester/medical plastics. The cuff fibers 26 are preferably coated with an antibacterial material that helps prevent bacterial growth at the venepuncture site 28. It is believed that the cuff fibers 26 also adhere well to adhesive tapes and film, etc., which further helps to prevent the intravenous catheter device 10 from dislodging (see FIG. 2). This is necessary because the area around a catheter site is often wet and slick from body and/or IV fluids, which makes it difficult to adhere adhesive film to medical tubing. The fibrous cuff 13 can also serve to demark the end area of the non-kinking tubing 11 for the person inserting the intravenous catheter device 10 (cuff stays external-outside the skin). Alternatively, the intravenous catheter device 10 does not have a cuff. Without the cuff, the intravenous catheter device 10 has a smooth outer surface that allows the non-kinking tubing 11 to be partially advanced into the patient's vein 35, where appropriate. Another alternative is a cuff 13 with a smooth, non-fibrous outer surface, which also allows the non-kinking tubing 11 to be partially advanced into the patient's blood vessel 35 behind the catheter portion 12 (cuff is internal-under the skin).

In the cuff 13 shown in FIG. 5, the spaced apart cuff fibers 26 project out from the cuff band 36 relatively evenly, preferably at an angle of between about 40 and about 50 degrees from the upper surface of the cuff band 36. Alternatively, the cuff fibers 26 may criss-cross one another as seen in FIG. 7, forming a tighter weave around the cuff band 36. The thick weave of the criss-crossed (interwoven) cuff fibers 26 of FIG. 7 is believed to soak up body and IV fluids rapidly and effectively.

In the intravenous catheter device 10 illustrated in FIGS. 8A-C, about one half of the cuff 13 is attached to the first end 16 of the intravenous catheter portion 12, and the other half or so of the cuff 13 is attached over the second end 15 of the non-kinking tubing 11. The first end 16 of the intravenous catheter portion 12 is attached to the second end 15 of the non-kinking tubing 11 end-to-end, so as to maintain a smooth bore that does not disrupt flow. The non-kinking tubing wall underlies the relatively smooth underside of the cuff band 36, as seen in FIGS. 8A-C. The underside of the cuff band 36 is preferably adhered to the outside of the end portion of the non-kinking tubing 11. As seen in FIGS. 8A-C, a first portion 51 of the cuff band 36 is attached to an outside end portion 53 by the first end 16 of the intravenous catheter portion 12, and a second portion 52 of the cuff band 36 is attached to an outside end portion 54 by the second end 15 of the non-kinking tubing 11.

Alternatively but not necessarily, the second end 15 of the flexible tubing 11 overlaps, and is attached to, the first end 16 of the intravenous catheter portion 12. The first catheter portion end 16 is preferably tapered and finished so as not to disrupt flow in the central channel. FIGS. 5 and 7 show cross-sections of the intravenous catheter device 10 across the cuff 13. In FIG. 5, the hollow needle 18, which is seen with its central channel 43, has not yet been withdrawn. As seen in FIG. 5, the outside surface of the intravenous catheter portion 12 below the cuff 13 contacts the inside surface of the non-kinking tubing 11 at the ends of the intravenous catheter portion 12 and the non-kinking tubing 11. The ends of the intravenous catheter portion 12 and the non-kinking tubing 11, whether end-to-end or overlapped, may be adhered to one another, or not. The cuff 13 may be glued on during manufacture using a suitable adhesive, and/or it may be press fitted.

Figure 3:
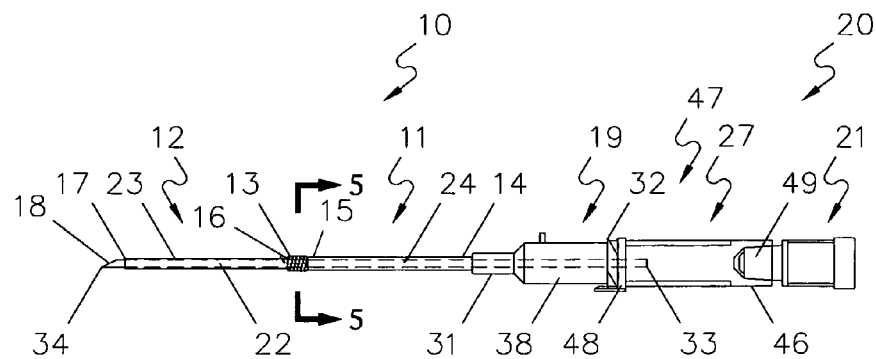
FIG. 3 is a perspective view of an intravenous catheter device according to the present invention.

The central channel 37 of the non-kinking tubing 11 and the channel 22 of the intravenous catheter portion 12 are substantially uniform, as seen in FIG. 3, so that flow is unimpeded. The channels 22, 37 are in fluid communication with one another and with the lumen of the patient's blood vessel 35 once the intravenous catheter device 10 has been placed. The blood vessel 35 may be in the patient's arm, hand, wrist, foot, leg, scalp, belly button, chest, or other site. The channels 22, 37 of the intravenous catheter portion 12 and the non-kinking tubing 11 are preferably substantially the same in diameter.

Finally, the intravenous catheter device 10 includes a needle 18 with a central channel 44, which is also called a cannula. Prior to use, the needle 18 extends through the intravenous catheter portion 12, non-kinking tubing 11, screw-on connector 19, and into the flash chamber 27. The needle 18 slides within the catheter device. The second end 34 of the needle 18 is sufficiently pointed to pierce the patient's skin and the underlying vein 35. The non-kinking tubing 11 between the intravenous catheter portion 12 in the patient's vein 35 and the screw-type connector 19 can be positioned and secured in a manner that allows for movement of the patient's joints, etc., without dislodgement or kinking.

Needles 18 that are between about 0.5 and about 3.0 centimeters longer then conventional catheter needles are preferred in the present invention in order to accommodate the length of non-kinking tubing 11 between the intravenous catheter portion 12 and the screw-type connector 19. A preferred intravenous catheter device 10 of the present invention is between about 0.5 and about 3.0 cm longer than a conventional intravenous catheter. The intravenous catheter portion 12 is preferably available in the following sizes: 24 gauge (about 0.7 millimeters); 22 gauge (about 0.9 millimeters); 20 gauge (about 1.1 millimeters); 18 gauge (about 1.3 millimeters); 16 gauge (about 1.7 millimeters); and 14 gauge (about 2.2 millimeters) OD (Outside Diameter).

Once the intravenous catheter device 10 has been placed, the intravenous catheter portion 12 lies under the patient's skin within the patient's body at the wrist, hand, arm, leg, foot, chest, scalp, etc ("internal"). The remainder of the intravenous catheter device 10 is located outside the venepuncture site 28 on the patient's arm, hand, leg, foot, scalp, chest, etc. (called here "external"). As seen in FIGS. 1, 2, and 6, the non-kinking, flexible tubing 11 is bent into a substantially curvilinear shape, preferably a U-shape or J-shape. This is done by the phlebotomist, registered nurse, or other healthcare practitioner who is in charge of placing the intravenous catheter device 10 for the particular patient. The J-shape or the like allows the external portion of the intravenous catheter device 10 to fit neatly along the patient's limb, etc. The non-kinking tubing 11 moves as the patient moves, continually conforming to the surface of the area of the body where it is located. The flexible tubing 11 need not be heated and cooled to force it to retain its shape once the curvilinear shape has been formed.

As seen in FIG. 2, the intravenous catheter device 10 is preferably secured to the patient's skin with a suitable securement membrane, pad, or film with an adhesive side, such as a transparent adhesive tape 30. The thin strip of sterile adhesive tape 30 is placed over the flexible tubing 11 adjacent to the point of insertion through the patient's skin. The adhesive tape, film, etc. may be of any suitable size or shape, depending on the particular application. The present intravenous catheter device 10 has a much lower profile than a conventional intravenous catheter and is much more likely to stay in place on the patient. The intravenous catheter device 10 of the present intravenous access device 10 does not require complicated added instructions and can easily be administered by healthcare practitioners.

The medical tubing connector is preferably a small screw-on/screw-off type of tubing connector 19. The word "connector" is meant to include tubing hubs, adapters, or receivers. The intravenous catheter device 10 is intended for use in conjunction with an IV bag (not shown) or a suitable medical fluid administration apparatus, such as an IV pump-type fluid dispensing machine. The purpose of the tubing connector 19 is to facilitate attachment: 1) of the needle/flash chamber to the intravenous catheter device 10; and, once the needle/flash chamber unit 47 has been retracted, 2) of the male tubing connector 50/IV fluid tubing 43 that leads up to the IV fluid administration apparatus.

Figure 4:
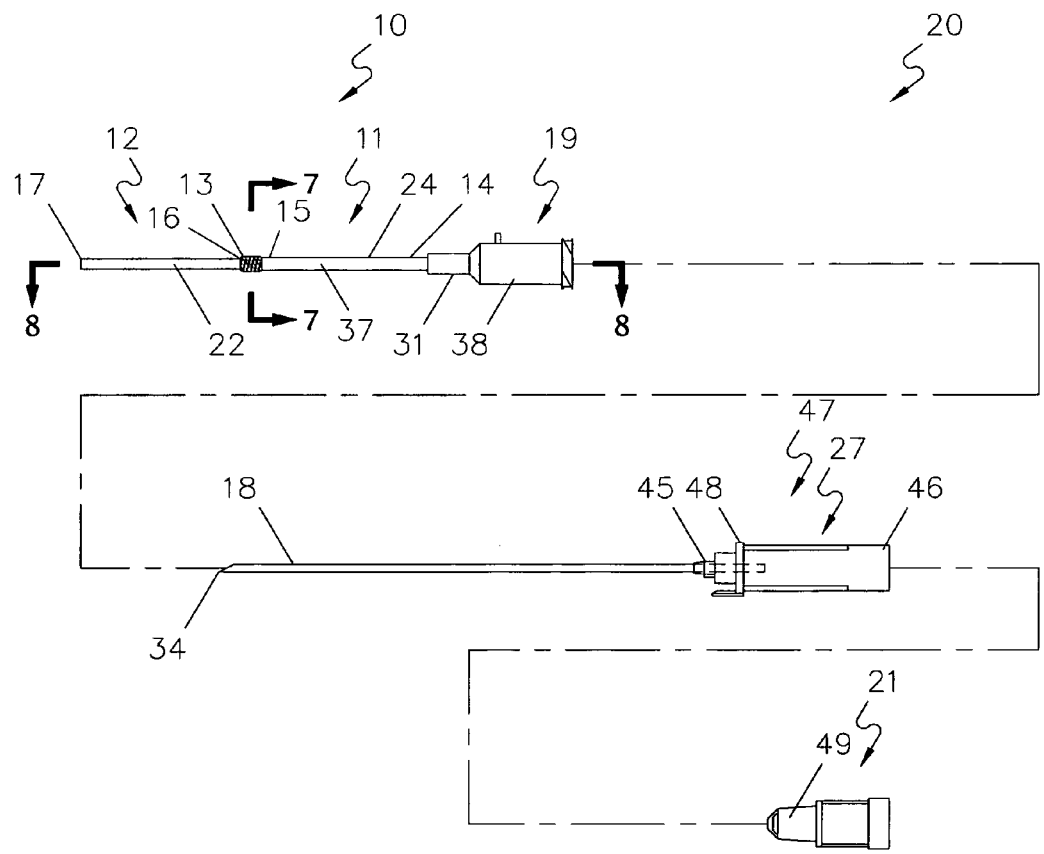
FIG. 4 is an expanded view of an intravenous catheter device according to the present invention.

As is depicted in FIGS. 1 through 4, the first end of the non-kinking tubing 11 fits in or on, and is attached to, the first end 31 of the small, screw-type connector 19. As seen in FIGS. 3 and 4, the packaged, ready-for-use intravenous catheter system 20 includes the intravenous catheter device 10, a needle/flash unit 47, and the end filter stopper 21. The separate needle/flash chamber unit 47 extends through the intravenous catheter device 10 prior to and during initial placement of the intravenous catheter in the vein or other vessel. In the needle/flash chamber unit 47, the first, non-piercing end 33 of the needle 18 is attached to the first end 45 of the clear, generally cylindrical-shaped flash chamber 27. In the packaged, ready-for-placement total system 20, the needle 18 of the needle/flash chamber unit 47 extends through the non-kinking tubing 11 and the intravenous catheter portion 12, with the pointed, second end of the needle extending out of the second end 17 of the intravenous catheter portion 12, as seen in FIG. 3. In constructing the total intravenous catheter system 20, the needle 18 is passed through the second end 32 and then the first end 31 of the screw connector 19, then the first end 45 of the flash chamber 27 passes through the second end 32 of the screw connector 19 and closely fits into the hollow in the screw connector 19, as seen in FIG. 3. On the outside of the flash chamber 27, a flange 48 rests against a similarly sized band on the second end 32 of the screw connector 19 when the needle/flash unit 47 is in place.

Lastly, a male end 49 of the end filter stopper 21 is inserted into the second end 46 of the flash chamber 27, as illustrated in FIG. 3. The remainder of the end filter stopper 21 seals the end of the flash chamber 27. The purpose of the transparent window in the flash chamber 27 is to permit the observer to see a slight back flush of blood once the lumen of the patient's blood vessel has been hit. This confirms for the healthcare practitioner that the lumen of the patient's vein has been accessed so he or she can proceed. Air can flow through the end filter stopper 21, but blood in the flash chamber 27 is prevented from flowing out (and making a mess) by the end filter stopper 21. Once the vein has been punctured and its lumen has been accessed, the needle/flash chamber unit 47 (and stopper 21) is retracted through the screw connector 19 end of the device, leaving the intravenous catheter portion 12, non-kinking tubing 11, and screw connector 19 of the intravenous catheter device 10 in place.

The needle/flash chamber unit 47 must be disposed of appropriately. The needle/flash chamber unit 47 preferably includes a conventional safety mechanism, such as one that retracts the withdrawn needle into the flash chamber or covers the piercing end of the withdrawn needle, to decrease the odds of the needle accidentally sticking the health practitioner, relatives of the patient, maintenance workers, etc.

Thus, the intravenous catheter system 20 includes: (1) the intravenous catheter device 10, which includes: (a) the screw-on, screw-off tubing connector 19; (b) the flexible, non-kinking, supported medical tubing 11, the first end 14 of the non-kinking tubing 11 being connected to the first end 31 of the screw connector 19; (c) the intravenous catheter portion 12 at the opposite, second end of the intravenous catheter device 10; the central channel 22 of the intravenous catheter portion 12 being in fluid communication with the channel 37 of the non-kinking, flexible tubing 11 when the intravenous catheter device 10 is in use; and (2) the removable needle/flash chamber unit 47, which includes: (a) the hollow needle 18; and (b) the flash chamber 27 at the first, non-piercing end 33 of the needle 18. The needle/flash chamber unit 47 is removable from the intravenous catheter device 10. The catheter system 20 preferably also includes: (3) the end filter stopper 21, which is inserted in the second end 46 of the flash chamber 27. The intravenous catheter device 10 preferably includes (d) a cylindrical-shaped cuff 13 connecting a second end 15 of the non-kinking tubing 11 to a first end 16 of the intravenous catheter portion 12.

When the catheter system 20 is assembled, the needle 18 extends through the central channel 22 of the intravenous catheter portion 12, and the central channel 37 of the non-kinking tubing 12. A portion of the needle 18 preferably extends through the center of the screw connector 19. The first end 45 of the flash chamber 27 closely fits into the second end 32 of the screw connector 19 when the needle/flash chamber unit 47 is in the intravenous catheter device 10. The first end 45 of the flash chamber 27 is attached to the first, non-piercing end 33 of the needle 18. The flash chamber 27 is in fluid communication with the central channel 44 of the needle 18 when it is in use, and a portion of the needle 18 extends through the screw connector 19 prior to retraction of the needle. When the intravenous catheter device 10 is in use, the central channel 22 of the intravenous catheter portion 12 is in fluid communication with the channel 37 of the non-kinking, flexible tubing 11. The second, pointed end 34 of the needle 18 extends through a second end of the intravenous catheter portion 12. The needle/flash chamber unit 47 is removed from the intravenous catheter device 10 once the second end 17 of the intravenous catheter portion 12 has been placed within the lumen of the patient's blood vessel 35.

After retraction of the needle 18 but before starting the flow of fluid to the patient, a first end of a length of IV fluid tubing 43 is normally attached to one end of a male tubing connector 50, as seen in FIGS. 1 and 2. The opposite end of the male tubing connector 50 is inserted in, press fitted, screwed onto, and/or otherwise attached to the second end 32 of the screw connector 19. Preferably but not necessarily, the male tubing connector 50 is inserted into a female second end 32 of the screw connector 19, and then a cylindrical shaped ring of the male tubing connector is screwed onto corresponding threads of the screw connector 19. The screw-type connector 19 is preferred for a leak-free fitting. The opposite end of the IV fluid tubing 43 is connected to the IV bag (not shown) or other delivery system for the IV fluids.

The intravenous catheter device 10 herein is not an appurtenance to a catheter nor is it a medical tubing holder. The present intravenous catheter device 10 does not include a hinge, a bracelet, or hook and loop straps. The intravenous catheter system 20 is not an external device for attachment to an existing catheter system. No external device, such as a clip, clasp, cover, or protector, is required to hold the shape of the non-kinking, flexible tubing 11. The non-kinking tubing 11 is simply bent into whatever position is considered most appropriate by the healthcare professional in charge of placing the intravenous catheter device for the particular patient. The non-kinking tubing 11 between the intravenous catheter portion 12 and the tubing connector 19 is flexible and not rigid. The intravenous catheter device 10 is not used in combination with other catheter devices. The non-kinking, flexible tubing 11, cuff 13, and attached intravenous catheter portion 12 of the present invention may be adapted for use in delivering fluids in other, like manner.

From the foregoing it can be realized that the described device of the present invention may be easily and conveniently utilized as an intravenous catheter device. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

BRIEF LIST OF REFERENCE NUMBERS USED IN THE DRAWINGS 10 intravenous catheter device
11 non-kinking tubing
12 intravenous catheter portion
13 cuff
14 first end of non-kinking tubing
15 second end of non-kinking tubing
16 first end of catheter portion
17 second end of catheter portion
18 needle
19 screw connector
20 total intravenous system
21 end filter stopper
22 catheter channel
23 catheter wall
24 non-kinking tubing wall
25 wire
26 cuff fibers
27 flash chamber
28 venepuncture site
29 patient's skin
30 adhesive tape
31 first end of screw connector
32 second end of screw connector
33 first end of needle
34 second, piercing end of needle
35 patient's blood vessel
36 cuff band
37 non-kinking tubing channel
38 channel of screw connector
39 mesh support arrangement
40 spiral support arrangement
41 rings support arrangement
42 support ring
43 IV fluid tubing
44 needle channel
45 first end of flash chamber
46 second end of flash chamber
47 needle/flash chamber unit
48 flash chamber flange
49 male end of end filter stopper
50 male tubing connector
51 first portion of cuff band
52 second portion of cuff band
53 outside end portion of catheter portion
54 outside end portion of non-kinking tubing

What is claimed is:

1. A method for inserting an intravenous catheter of an intravenous catheter device, the method comprising:
inserting a removable needle from an intravenous catheter device into a patient's vein, the intravenous catheter device comprising a medical tubing connector, a length of flexible, non-kinking, supported medical tubing, and the removable needle, wherein a first end of the length of flexible, non-kinking, supported medical tubing is joined to the medical tubing connector and a second end of the length of flexible, non-kinking, supported medical tubing is joined to an intravenous catheter portion having a diameter of from about 0.7 millimeters to about 2.2 millimeters, and wherein the medical tubing connector, the length of flexible, non-kinking, supported medical tubing, and the intravenous catheter portion each define a channel in fluid communication with one another, the removable needle passing through each channel and extending from the intravenous catheter portion as it is being inserted into the patient's vein;
inserting the intravenous catheter portion into the patient's vein after insertion of the removable needle;
withdrawing the removable needle from the vein after insertion of the intravenous catheter portion;
bending the length of flexible, non-kinking, supported medical tubing after withdrawing the removable needle from the vein and securing the bent length of flexible, non-kinking, supported medical tubing to the patient, wherein the bent length of flexible, non-kinking, supported medical tubing does not require an external device to hold open the length when bent in a curvilinear shape, at least a portion of the length of flexible, non-kinking, supported medical tubing being outside of the patient's vein; and
dispensing fluid into the intravenous catheter device after insertion of the intravenous catheter portion in the patient's vein such that the fluid travels through each channel into the patient's vein.

2. A method as in claim 1, wherein the length of flexible, non-kinking, supported medical tubing comprises a wire mesh within a wall of the length of flexible, non-kinking, supported medical tubing.

3. A method as in claim 1, wherein the non-kinking supported tubing comprises a plastic netting within a wall of the non-kinking tubing; and wherein the non-kinking tubing and the intravenous catheter portion are about equal in length.

4. A method as in claim 1, wherein the non-kinking supported tubing comprises a flexible tubing support arrangement incorporated within a wall of the non-kinking tubing.

5. A method as in claim 1, wherein the bent length of flexible, non-kinking, supported medical tubing has a U-shape.

6. A method as in claim 1, wherein the bent length of flexible, non-kinking, supported medical tubing is secured to the patient by tape.

7. A method as in claim 1, further comprising disposing of the removable needle.

8. A method as in claim 1, wherein intravenous catheter device further comprises a cylindrical-shaped cuff attached to an outside of the intravenous catheter portion adjacent the second end of the length of flexible, non-kinking, supported medical tubing.

9. A method as in claim 8, wherein the cuff comprises a cylindrical-shaped cuff band and a plurality of cuff fibers, an end of each of the plurality of cuff fibers being attached to the cuff band, the plurality of cuff fibers extending outwardly from the cuff band.

10. A method as in claim 8, wherein the cuff comprises a cylindrical-shaped cuff band and a plurality of cuff fibers, an end of each of the plurality of cuff fibers being attached to the cuff band, the plurality of cuff fibers being substantially criss-crossed with one another.

11. A method as in claim 8, wherein the intravenous catheter portion is attached to the second end of the length of flexible, non-kinking, supported medical tubing end-to-end, the length of flexible, non-kinking, supported medical tubing underlying the cuff band, wherein a first portion of the cuff band is attached to an outside end portion of the intravenous catheter portion and a second portion of the cuff band is attached to the outside end portion of the length of flexible, non-kinking, supported medical tubing.

\* \* \* \* \*